(12) United States Patent
Baumann et al.

(10) Patent No.: US 6,978,657 B1
(45) Date of Patent: *Dec. 27, 2005

(54) PORTABLE CHEMICAL DETECTION SYSTEM WITH INTERGRATED PRECONCENTRATOR

(75) Inventors: Mark J. Baumann, Albuqueruqe, NM (US); Charles A. Brusseau, Tijeras, NM (US); David W. Hannum, Albuquerque, NM (US); Kevin L. Linker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 62 days.

This patent is subject to a terminal disclaimer.

(21) Appl. No.: 10/306,939

(22) Filed: Nov. 27, 2002

Related U.S. Application Data

(63) Continuation-in-part of application No. 09/339,349, filed on Jun. 23, 1999, now Pat. No. 6,523,393, which is a continuation-in-part of application No. 09/410,976, filed on Oct. 4, 1999, now Pat. No. 6,572,825.

(51) Int. Cl.[7] .............................. G01N 1/40; G01N 7/16
(52) U.S. Cl. ................. 73/28.04; 73/31.07; 73/863.11; 73/863.23
(58) Field of Search ......................... 73/28.04–28.06, 73/31.01, 31.02, 31.07, 863.11, 863.12, 864.81, 73/863.23; 422/88; 250/288

(56) References Cited

U.S. PATENT DOCUMENTS

| | | | | |
|---|---|---|---|---|
| 4,633,083 A * | 12/1986 | Knorr et al. | ................. | 250/282 |
| H00406 H * | 1/1988 | Wohltjen | ..................... | 436/153 |
| 5,014,541 A * | 5/1991 | Sides et al. | ................. | 73/23.41 |
| 5,571,976 A * | 11/1996 | Drolet | ..................... | 73/864.71 |
| 5,789,745 A * | 8/1998 | Martin et al. | ................ | 250/286 |
| 5,854,431 A * | 12/1998 | Linker et al. | ............. | 73/863.23 |
| 5,915,268 A * | 6/1999 | Linker et al. | ................. | 73/23.2 |
| 6,085,601 A * | 7/2000 | Linker et al. | ............. | 73/863.12 |
| 6,334,365 B1 * | 1/2002 | Linker et al. | ............. | 73/864.81 |
| 6,523,393 B1 * | 2/2003 | Linker et al. | ............. | 73/28.02 |
| 6,572,825 B1 * | 6/2003 | Linker et al. | ............. | 422/82.01 |
| 2003/0122068 A1 * | 7/2003 | Berking et al. | ............. | 250/288 |
| 2003/0155506 A1 * | 8/2003 | Motchkine et al. | ......... | 250/288 |

\* cited by examiner

*Primary Examiner*—Hezron Williams
*Assistant Examiner*—John C Hanley
(74) *Attorney, Agent, or Firm*—Robert D. Watson; George Libman

(57) ABSTRACT

A portable system for the detection of chemical particles such as explosive residue utilizes a metal fiber substrate that may either be swiped over a subject or placed in a holder in a collection module which can shoot a jet of gas at the subject to dislodge residue, and then draw the air containing the residue into the substrate. The holder is then placed in a detection module, which resistively heats the substrate to evolve the particles, and provides a gas flow to move the particles to a miniature detector in the module.

30 Claims, 5 Drawing Sheets

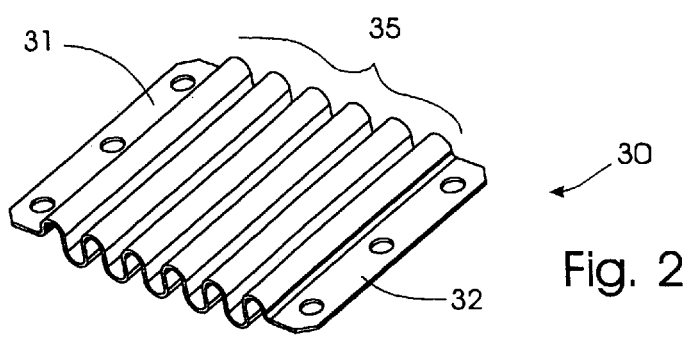
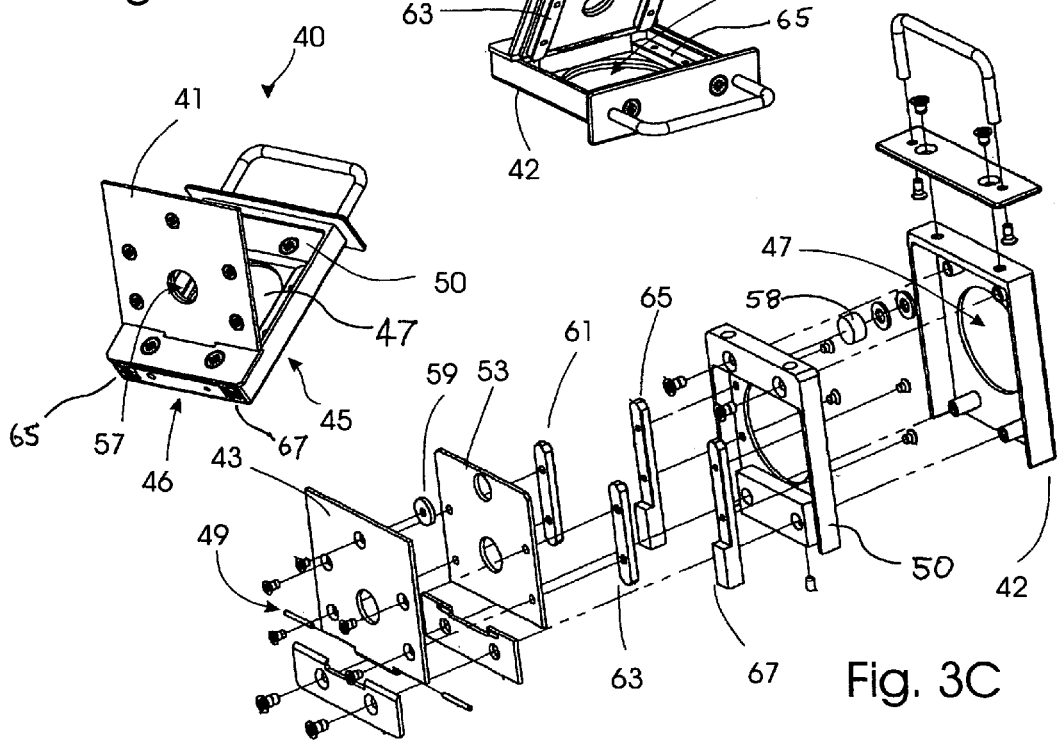

US 6,978,657 B1

PORTABLE CHEMICAL DETECTION SYSTEM WITH INTERGRATED PRECONCENTRATOR

CROSS REFERENCE TO RELATED APPLICATIONS

This application is a Continuation-In-Part of Ser. No. 09/339,349 now U.S. Pat. No. 6,523,393, filed Jun. 23, 1999, and Ser. No. 09/410,976 now U.S. Pat. No. 6,572,825, filed Oct. 4, 1999.

The United States Government has rights in this invention pursuant to Department of Energy Contract No. DE-AC04-94AL85000 with Sandia Corporation.

BACKGROUND OF THE INVENTION

This invention relates to the field of particle concentrators, and more particularly to an apparatus and method for capturing and transporting to an analyzer target chemical substances adherent to a substrate that either has been rubbed on the surface of a test subject to test for the presence of the target chemical substances or has been exposed to a vapor. Preconcentration of the target substances results from the accumulation of the substrate on the test surface. Specifically, according to the invention, target substances thus preconcentrated are removed (or, as the term is used herein, "evolved") from the substrate by heating the substrate in the presence of suction or other gas flow for movement to a chemical analyzer such as a portable ion mobility spectrometer. Resistive heating is accomplished by passing current through the metallic substrate. For purposes of this disclosure, including the appended claims, "suction" in association with the chemical analyzer is intended to include all modalities through which gases are caused to pass from outside of the analyzer to inside the analyzer, regardless of whether the fan or other means for causing the flow of gases into the analyzer resides inside the analyzer or external to it. The apparatus of the invention is suited to human portability and is especially useful in conjunction with detecting compounds such as explosives, illegal drugs, other controlled substances and chemical agents. For purposes of this application, in the context of describing the claimed invention, the term particle is intended not to exclude vapor.

Additional background information, supplemental to the information provided here, is found in U.S. Pat. No. 5,854,431 "Particle Preconcentrator", U.S. Pat. No. 6,085,601 "Particle Preconcentator", and in pending U.S. patent application Ser. No. 09/339,349, now U.S. Pat. No. 6,523,393 "Human Portable Preconcentrator System", all of which are incorporated by reference herein in their entirety.

The detection of explosives, narcotics or other chemicals is a growing part of contraband detection. Recent years have seen rapid development of detectors capable of identifying the presence of explosives by capturing and identifying either vapors emanating from explosive materials or particles of explosive material, or both. Similarly, such detectors can also identify vapors and particles associated with other forms of contraband such as illegal drugs and other controlled substances. Such vapors and particles associated with contraband may be present and detectable on or near persons or objects that have been exposed to contraband materials and substances. Suitable detectors for this purpose include, but are not limited to, ion mobility spectrometers (IMS), electron capture detectors, mass spectrometers (MS), and chemiluminescence-based systems.

Detection of explosives, narcotics or other contraband substances demands reliable and convenient means for collecting and analyzing sample. The '431, '601 and '393 patents mentioned above are examples of ways to collect trace amounts of target chemical in dilute concentration in gases. The present invention provides an efficient, portable system for either detecting the swiped substances or for collecting vapor samples and subsequently detecting those samples.

Swiping surfaces in order to concentrate sample is well known in the art of chemical detection. However, a challenge remains in how to reliably analyze chemicals collected and concentrated using the swiping approach, especially so that analysis results can be obtained quickly in a field setting. The present invention offers a quick and reliable method and apparatus to capture the target chemicals collected using the swiping technique and to deliver those chemicals to an analyzer for detection. An important aspect of the invention is that heat is used in a controlled fashion to drive off chemicals adherent to the swiped substrate. For purposes of this disclosure, the term "evolve" is used in conjunction with the process whereby target chemicals are driven off of the substrate as a consequence of application of heat.

SUMMARY OF THE INVENTION

It is an object of this invention to provide a person-portable system for collecting and detecting chemical particles.

To achieve the foregoing and other objects, and in accordance with the purpose of the present invention, as embodied and broadly described herein, the invention may include a substrate for collecting particles and a substrate holder comprising a pair of opposed panels, at least one of the panels having a front aperture. The substrate may be tightly held between the panels with its collection surface facing the front aperture. A detector module has an opening for receiving the substrate holder along a detection gas path for carrying gas from the front aperture to an ion mobility spectrometer having an input connected to the detection gas path and a drift gas generating system for providing drift gas to said ion mobility spectrometer.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

FIG. 2 is a perspective view of an embodiment of a substrate for use in this invention.

FIGS. 3A, 3B and 3C are open, closed and exploded views, respectively, of a holder for the substrate of FIG. 2.

DETAILED DESCRIPTION OF THE INVENTION

The present invention represents an improvement over earlier art in the area of target chemical substance collection and preconcentration. The invention provides for convenient removal, capture and analysis of chemical substances from test surfaces that adhere to a substrate. It is suited to field applications, and specifically, hand held or otherwise human portable use, as it employs a simple, lightweight heating device that easily adapts to existing hand-held portable detection machines such as a portable IMS. It is also suited to use with DC power sources well known in the field of portable electronic systems.

Fundamentally, the invention uses electrical current passed through a porous metallic substrate on which target chemical substances may be present, to heat the substrate and cause those substances to evolve into a region of controlled gas flow. Substances caused to evolve in this way are easily carried directly to a detector. If the substrate is swiped over a subject under test, the substrate may be carried in a holder that provides for easy insertion and removal of the substrate into a relatively small, person-portable, detection device. The detection device also may be used to dislodge particles and vapor from a subject under test and to attract these substances into the device and onto the substrate.

Figure 1:
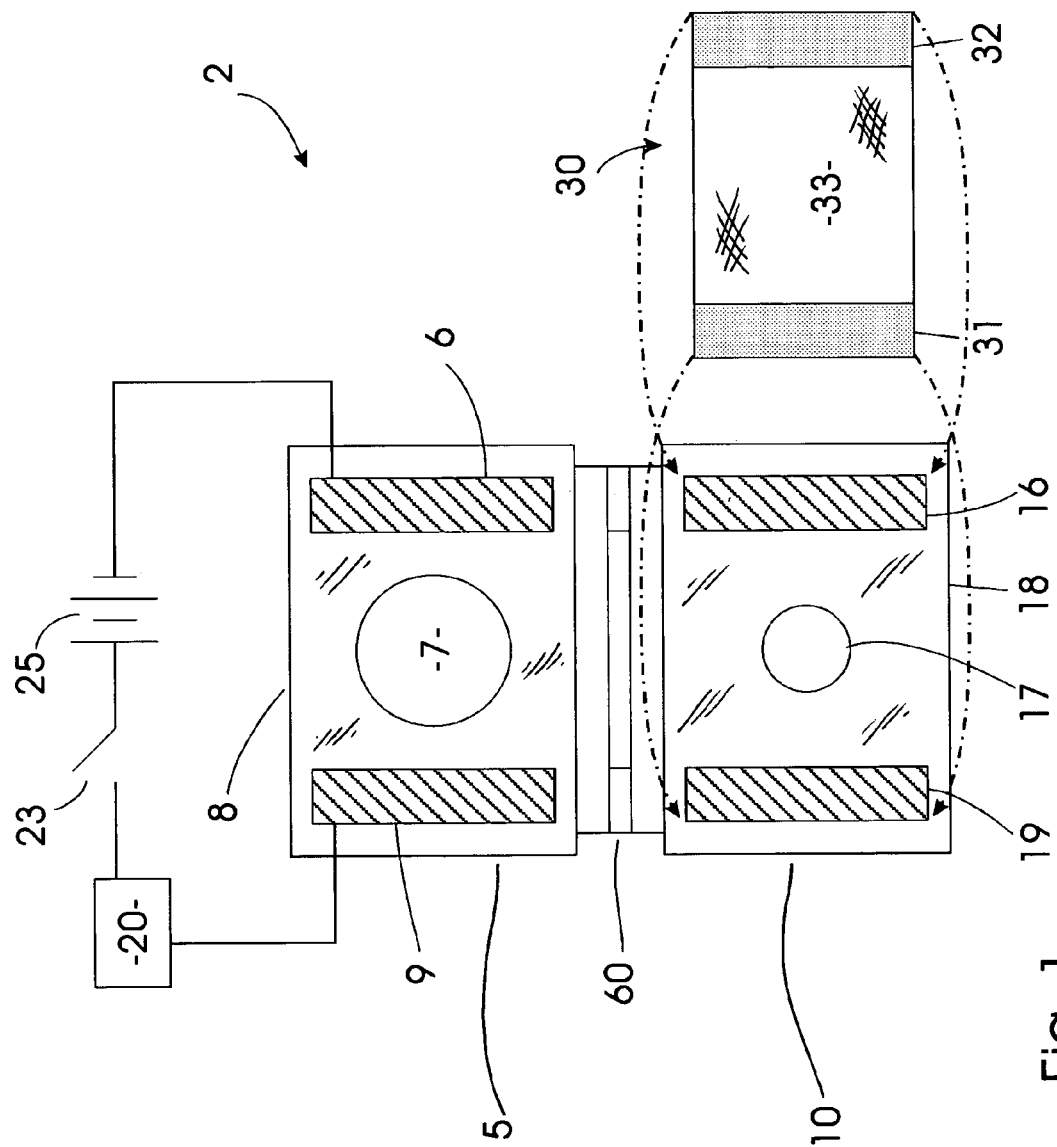
FIG. 1 is a schematic diagram showing some of the electrical features of the invention

Referring to FIG. 1, a substrate holder 2 is seen to comprise two panels 5 and 10 pivotally connected to each other along one edge by a hinge 60 in a well-known manner. Panels 5 and 10 are shown in an open position ready to receive a substrate 30, which comprises a formed porous metallic member as discussed hereinafter. In the closed position, the opposing edge 8 of panel 5 is adjacent opposed edge 18 of panel 10, and substrate 30 is held between the panels like a page between two covers of a book. The first panel 5 includes a front aperture 7 located generally in the central region of the panel. Aperture 7 may be of any shape and is preferably sized sufficiently large to expose a relatively large portion of the substrate. The second panel 10 may have a back aperture 17, which aperture may be smaller than aperture 7. As discussed hereinafter, the purpose of aperture 17 is to permit air to be drawn through the substrate in holder 2. If aperture 17 is not present, means such as spacers between the edges of the substrate and panel 10 must be provided for air to circulate between the substrate and the surface of panel 10.

The surfaces of each panel facing the substrate 30 contain at least one matched pair of spaced blocks 6, 9 and/or 16, 19. As described hereinafter, these blocks serve to hold and make electrical contact with substrate 30. Blocks 16, 19 also permit an air space to exist between substrate 30 and panel 10 if no aperture 17 has been provided.

As shown, each of these blocks extends in one direction for approximately the length of one dimension of its panel. It is made thick enough to space the substrate 30 from its panel (if necessary), and wide enough to provide a good contact with the edges 31, 32 of substrate 30 without blocking too much of the surface 33 of the substrate 30. Each panel has a pair of spaced blocks, and opposing blocks 6, 16 and 9, 19 are arranged to align with each other when holder 2 is in the closed position.

One of the principal uses of these blocks is to function as electrical contacts to metallic substrate 30. As discussed above, vapor is evolved from a substrate by passing current through to resistively heat substrate 30. The electrical resistance of substrate 30 is on the order of 0.1 ohm, and the current through substrate 30 may be 10's of amps. Therefore, the resistance between substrate 30 and the electrical power circuit connected thereto must be significantly less than 0.1 ohm to prevent destructive arcing. Accordingly, as shown in FIG. 1, at least one of each pair of blocks 9, 19 and 6, 16 is an electrical conductor such as copper that is connected to one of two poles of a power supply such as battery 25.

As illustrated, the battery is connected to at least two blocks on opposite sides of aperture 7, such as one of 6, 16 and one of 9, 19, which blocks contact opposite ends 31, 32 of substrate 30. When holder 2 is closed, substrate 30 is sandwiched between blocks 6, 16 and between blocks 9, 19. One pair of the blocks, such as blocks 16, 19, may be of any hard material if they are not connected to the power supply; they should be an electrically conductive material if they are connected to the power supply. Each pair of blocks should be of approximately the same area and aligned in order to maximize the surface area in contact with substrate 30, and thereby minimize contact resistance as discussed above.

The invention method and apparatus require that the substrate be heated sufficiently to cause target chemicals to evolve, but not so much as to unnecessarily degrade the substrate. It is believed that for most target chemicals, the substrate can be heated sufficiently to drive off all target analyte, leaving the substrate clean for future use. For target chemicals such as TNT, RDX and various narcotic substances, the inventors have experienced success in detection by heating the substrate to within the range of 100° C. to 200° C., with the best results occurring between 150° C. and 200° C. The optimal temperature, however, for causing chemicals to evolve from the substrate will depend on the target chemicals, themselves.

Alternatively, although not shown, non-conductive blocks 16, 19 could be eliminated and blocks 6,9 could push substrate 30 directly against panel 10, or raised portions on panel 10 that emulate blocks 16, 19.

Also shown in FIG. 1 are a DC power supply 25, a heating control 20 and a switch 23 for activating the circuit. In the preferred embodiment, the heating control 20 may be a computer device such as a personal digital assistant (PDA) that is programmed to control the current through substrate 30 as discussed hereinafter.

It is possible to include features in the panels, for example, to optimize the flow of air and other gases through the porous substrate 30 and into the detector 94. It has been observed by the inventors, though, that favorable results are obtained in field-type applications, even without special air flow configurations beyond what has been described here. There is enough leakage around the various components that gases flow easily through the substrate, via the aperture, into the detector, resulting in favorable detection results.

FIG. 2 illustrates a substrate 30 for use in the gas-transport mode of the invention. As described in the aforementioned '349 patent application, substrate 30 may be a porous (to gas) metal fiber such as a continuous sheet of Bekipor® metal fiber. In this embodiment, two opposed flat edges 31, 32 of a sheet of Bekipor® ST 40BL3 metal fiber lie in a plane, and the remainder of the sheet 33 has been folded into a plurality of pleats 35 extending symmetrically about the plane. The cross-section of each pleat is rounded. This design provides a large surface area for the collection of a substance, and also has a minimum of crevasses into which particles may become lodged such that they would not readily evolve from substrate 30. In one embodiment, the overall length of substrate 30 is about 2 inches, the width (and length of edges 31, 32) is about 1.5 inches, the width of each flat edge 31, 32 is about 0.25 inch, and the thickness (peak-to-peak height of a pleat) is about 0.25 inch.

In the swipe mode of the invention, where the substrate is physically rubbed against the test surface, substrate 30 does not need the pleats of the substrate of FIG. 2 and may be planar as indicated in the substrate of FIG. 1. This substrate is preferably of the same material as the pleated substrate discussed above, although other materials may require alternative means for heating the substrate to evolve the adhered particles.

As shown in FIGS. 3A, 3B and 3C, holder 40 provides a structure for rigidly holding substrate 30 and includes a rigid case 42 that surrounds a heat-resistant, electrically insulated, shell 50 that forms an inner box within case 42. Case 42 is preferably made of a metal that does not attract explosive particles such as stainless steel, while shell 50 is preferably formed of nonconducting material such as Teflon®. The interior of shell 50 is slightly larger than substrate 30.

One side 45 of holder 40 is an integral part of case 42 and shell 50 and contains a hole 47 corresponding to hole 7 of holder 2 of FIG. 1. The other side of holder 40 is a door 41 that is preferably connected to holder 40 by a hinge 49 and which includes an outer case portion 43 and shell portion 53 which are compatible with the materials of case 42 and shell 50. Door 41 further comprises a hole 57 corresponding to hole 17 of holder 2, and a latch 59 for holding door 41 in a closed position. Preferably, latch 59 may comprise a steel plate attached to door case 42 and embedded in a hole in door shell 53, and a magnet 58 embedded within case 42 at a location aligned with the steel plate when the door is closed. Of course, any other latch may be utilized in the practice of the invention. Furthermore, other door construction known in the art (such as no hinge and two magnetic latches) may be utilized in the invention.

Holder 40 contains a pair of spaced blocks 61, 63 on door shell 53 and a pair of aligned blocks 65, 67 on shell 50. As discussed above, at least one of blocks 61, 65 on one side of substrate 40, and at least one of blocks 63, 67 on the other side of substrate 40, must be electrically conductive and connected to a voltage source. In a preferred embodiment, the bottom 46 of holder 40 is formed by insulating shell 50 and is not covered by metal case 42. Each of metal blocks 65, 67 extend through bottom 46 as electrical contacts such as receptacles for pin connectors on the housing into which holder 40 is placed. Any other manner of connecting a voltage source to the blocks may also be utilized in the practice of the invention.

The width of the edges 31, 32 of substrate 30 corresponds to the width of blocks 61, 63, 65, 67 in holder 40, permitting a low resistive electrical contact with substrate 30 when it is placed within holder 40 and door 41 is closed. Since the function of latch 59 is mainly to keep door 41 closed to prevent the loss of substrate 30 as holder 40 is moved, as will be discussed hereinafter, the device 60 into which holder 40 is placed provides additional pressure against holder 40 to ensure a good electrical contact is made with substrate 30.

Figure 4:
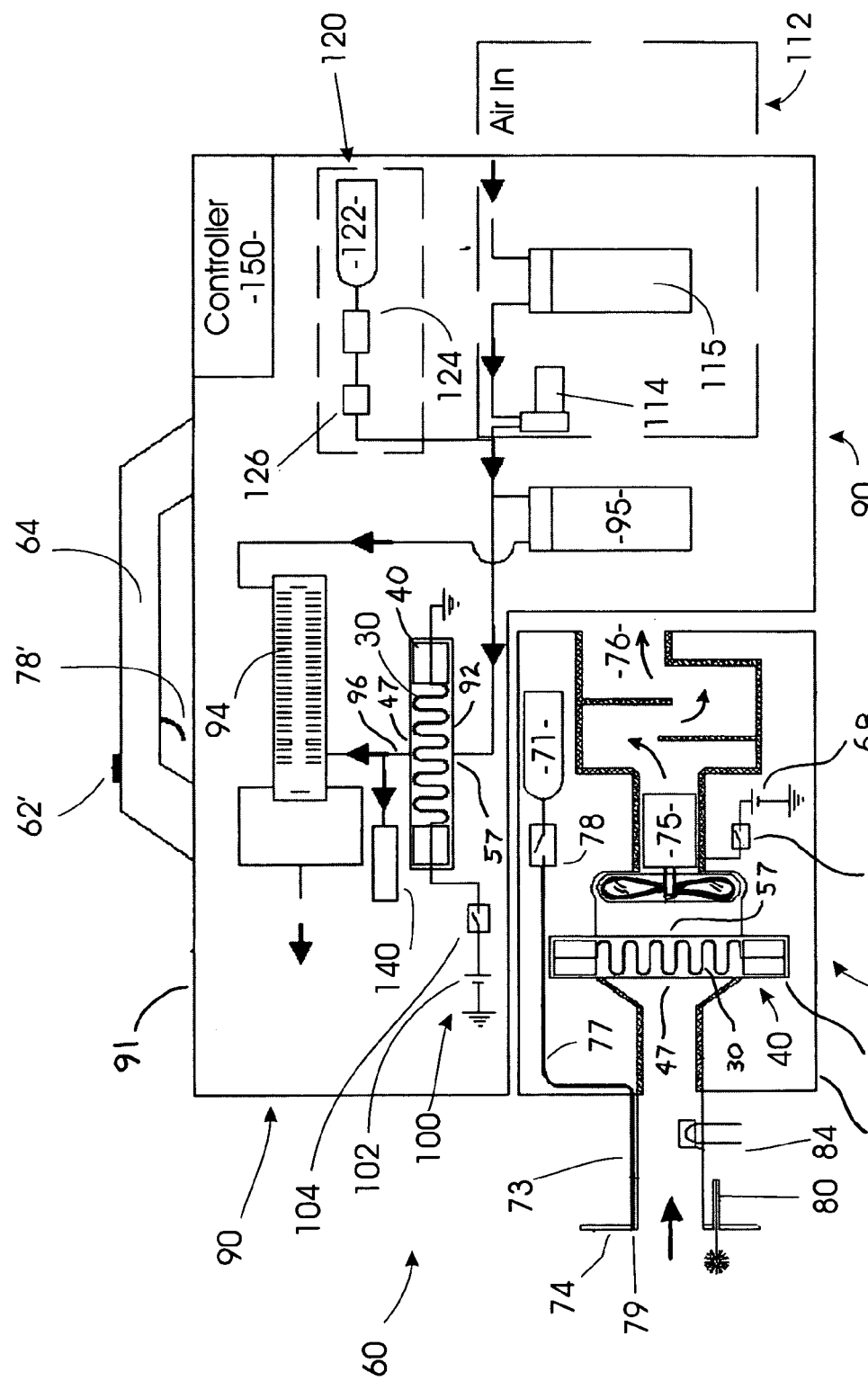
FIG. 4 is a schematic view of a device utilizing the holder of FIGS. 3A, 3B, 3C.

The device 60 in which holder 40 is utilized is shown in FIG. 4 to include a collection module 70 for pulling vapor through substrate 30 and a detection module 90 for determining the presence of detectable substances that were either drawn to or swiped on substrate 30. These modules may either be separable (as illustrated schematically in FIG. 4) or built into one unit (as illustrated schematically in FIG. 6), and typically powered by a battery carried within the respective modules. The longest dimension of either module is about 12 inches, and the total weight of either module (including battery) is less than 20 pounds.

Collection module 70 is simply a case 89 with a hollow tube 73 extending from the case 89, with holder 40 and substrate 30 fitting within a slot 87 in the case 89 such that hole 47 of holder 40 is aligned with the interior end of tube 73. An electrically driven fan 75 pulls air along a collection gas path into device 70 through tube 73 and expels the air through an exit aperture 76 using technology well known in the small vacuum cleaner art.

The end of tube 73 includes a flat flange 74 extending radially therefrom. During testing of an earlier embodiment of the invention, it was noticed that some air flow into tube 73 followed the outer surface of tube 73 until it was drawn into the open end toward fan 75. Flange 74 is utilized to disrupt that air flow, thereby increasing the ability of module 70 to draw particles and vapor from a subject in front of the opening of tube 73.

It has also been determined that particles often tend to adhere to the surface which carries them. For several years, Sandia National Laboratories portal detector, described in U.S. Pat. Nos. 5,915,268 and 6,334,365, has provided puffs of air to dislodge particles from a person being screened. That capability has been extended to collection module 70 by a common $CO_2$ cylinder 71 of a type conventionally used for compressed gas applications like paint ball guns, air pistol, portable tire inflation, etc. An examples of such a cylinder include Brass Eagle, Inc. part # 7125 or 1304. The output of cylinder 71 is connected by narrow tubing 77 through an actuator 78 to an end 79 extending through flange 74 adjacent the opening of tube 73.

In operation, device 60 may be held by handle 64 near a subject to be tested and a switch 62 closed by button 62' on handle 64 to power fan 75 from battery 68. A trigger 78' may be momentarily closed to cause actuator 78 to close, which permits a blast of gas from cartridge 71 to exit tubing 77 at end 79 and dislodge any particles on the subject adjacent tube 73. Such actuators for momentary blasts of pressure from a $CO_2$ cartridge are well known in the air pistol and paint-ball dispensing fields. The lowered air pressure at the entrance of tube 73 causes the dislodged particles to be drawn through tube 73 to substrate 30 in holder 40.

To help the operator properly aim tube 73 in low light situations, a laser pointing device 80 may be affixed to tube 73. The laser pointing device helps the operator identify the general location that is being sampled.

The substrate 3 is heated to evolve the substance, and a small volume of air moves the particles to a detector. For this invention, the components of the module have been improved.

To help the operator determine if swipe alone, either swipe or vapor, or vapor alone will provide adequate chemical sampling, a temperature sensor 84 is included. The sensor 84 is located such that ambient air temperature can be accurately identified and conveyed to the operator through the PDA. Vapor collection is not reliable below about 22° C., and swipe collection is not reliable above about 40° C. Depending on the chemical of interest and ambient temperature, software within the PDA will recommend a sampling method to be utilized.

Once a substrate 30 has been exposed to a test subject either by swiping or by collection module 70, and placed in a holder 40 if swiped, the holder 40 is placed into an opening 92 in the case 91 of detection module 90. Detection module 90 consists of a detector 94 for detecting a substance of interest on substrate 30, a substrate heating system 100 for evolving the substance from substrate 30, and an air mover for moving the substance along a detector gas path 96 from substrate 30 to a detector 94. FIG. 4 shows two possible air movers; a fan system 112 and a gas system 120. Only one air mover is utilized in the practice of the invention. Each air mover provides a stream of clean air that enters holder 40 through opening 57 so that particles which adhered to the side of substrate 30 that is adjacent hole 47 do not have to pass through substrate 30. Rather, once evolved from substrate 30, they pass back through hole 47 to detector 94.

The detection module 90 may comprise a miniature ion mobility spectrometer 94 such as the device described by K. Pfeifer et al., "Miniaturized Ion Mobility Spectrometer System for Explosives and Contraband Detection", Sandia National Laboratories, SAND2002-2247C, presented August 2002. The IMS tube is constructed from ceramic dielectric with 0.5 mm Ni electrodes separated by 0.25 mm sapphire washers to form the drift tube, which is 10 mm on a side, has a drift length of 36 mm, and an overall length of 54 mm. Ions are formed from eight 0.9 Ci $Am_{241}$ $\alpha$ particle sources and the electric field is formed such that negative ions are accelerated toward the right. A Faraday plate in the end cap serves as the pickup and is embedded under the inlet tube for drift gas from a methylene chloride canister 95. The interior diameter of the drift tube is 6 mm in diameter with a 3 mm aperture to limit ions to the center of the tube. The electric field magnitude of 19 kV/m is formed from a series resistor network, and the field direction is to the left.

Alternatively, or in combination with ion mobility spectrometer 94, detector 90 may comprise a chemlab-on-a-chip 140, a miniature detector that provides an electrical output when a test substrate detects a particular substance. (See, for example, R. Hughes et al., *Chemical Sensing with an Integrated Preconcentrator/Chemiresistor Array*, 200th Meeting of The Electrochemical Society held Sep. 2–7, 2001 in San Francisco, Calif.) The use of two different detectors would reduce false error readings as the outputs from each of detectors 94 and 140 could be evaluated by controller 150 which could be programmed to provide an indication of explosive detection only if both detectors detected the same material.

Substrate heating system 100 includes a source of electrical energy such as battery 102 connected to one side of substrate 30 through blocks of holder 40 as discussed above. The other side of substrate 30 is connected to ground. A switch 104, actuated by a controller 150, which preferably is a programmable PDA or equivalent device, is provided in series with the battery 102 and substrate 30. When it is desired to evolve substances from substrate 30, switch 104 is closed for a sufficient time to heat substrate 30 to a proper temperature. The controller 150 monitors the energy dissipated in substrate 30 by measuring current and voltage drop as a function of time, and increases the 'on' time to compensate for a decrease in battery voltage.

Air mover 112 includes a small pump 114 having an output connected to hole 57 in holder 40. The input of pump 114 is connected to a gas purifier 115 such as conventionally housed in a canister made by the W A HAMMOND DRIERITE Co., Xenia, OH, and sold under the name 'Drierite'. The output of pump 114 is on the order of 50 standard cubic centimeters per minute for this application.

Alternative air mover 120 consists of another $CO_2$ cartridge 122 having an output connected to a valve 124 that may be controlled either by controller 150 or the operator through conventional means. The output of valve 124 feeds through a pressure regulator 126 to reduce the output to about 50 SCCM for application to hole 57 of holder 40.

The air path from hole 47 to the detector 94 is also heated to 80–100° C. to ensure that particles do not adhere to the walls of the path. In addition, the output from either air mover also provides an input to the methylene chloride canister 95, which canister provides drift gas for the IMS 94, as discussed above.

Figure 5:
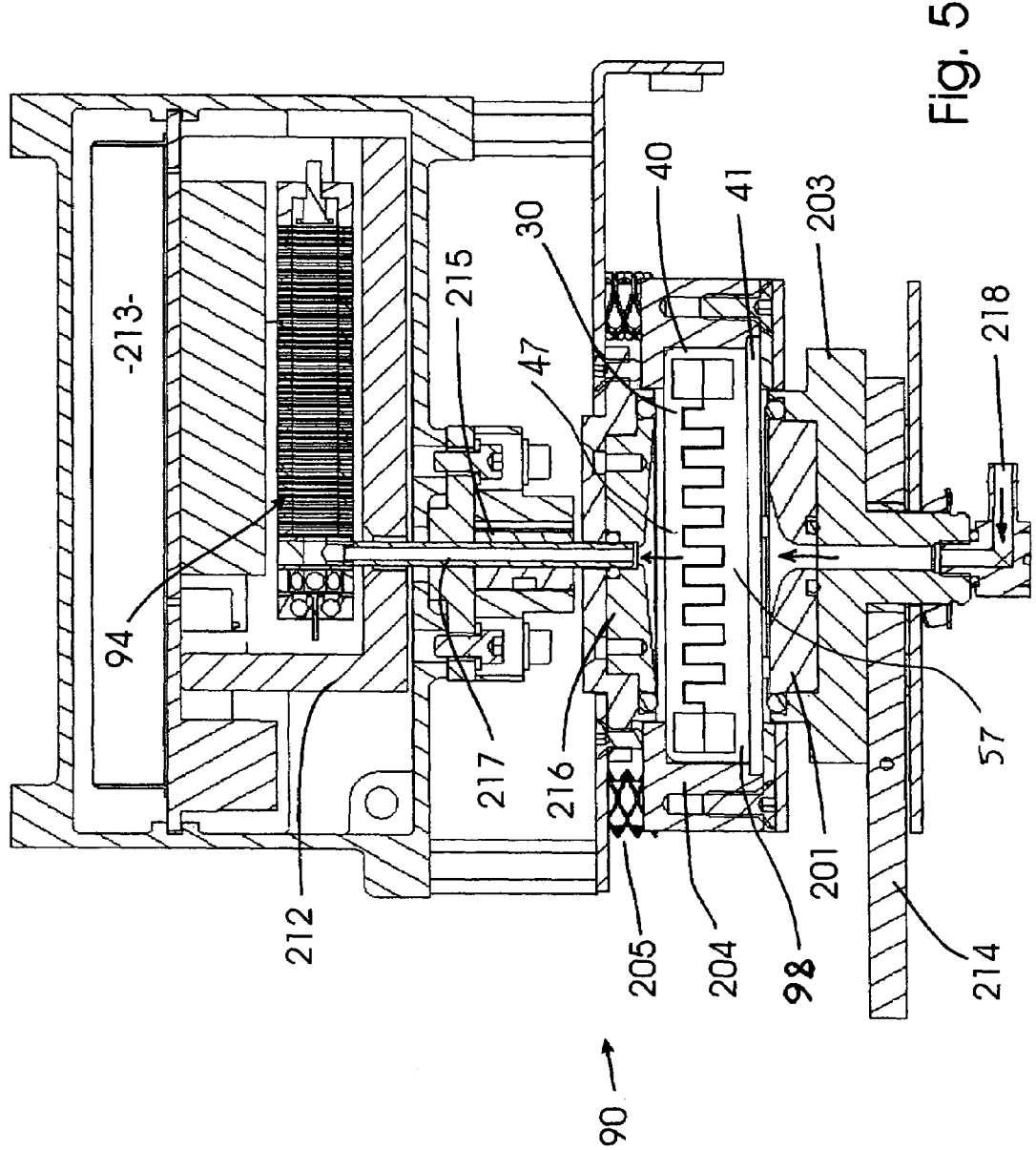
FIG. 5 is a cut-away view of a preferred embodiment of the device of FIG. 4.

FIG. 5 shows a portion of a preferred embodiment of the detection module 90. An IMS 94 is surrounded by heat insulating blocks 212, 213. An input tube 217 extends from a front horn 216 that defines a plenum against the surface of a holder 40 that contains a substrate 30. A heater block 215 that is controlled by controller 150 heats tube 217 and discussed above. Hole 47 is in the side of holder 40 facing front horn 216; hole 57 faces another tube 218 through a back horn 201 and a back sealing ring 203. Tube 218 is an input from the air mover 210 (not shown).

Holder 40 slidably fits in a pocket 98 in guide 204 that aligns with a slot 92 in the case 91 of detection module 90. When handle 214 is rotated into the figure, a camming action is provided by roller bearings (not shown) that press sealing ring 203 and back horn 201 firmly against door 41 of holder 40. This pressure causes guide 204 to compress springs 205 as it carries holder 40 firmly against front horn 216. The pressure against door 41 keeps substrate 30 in good electrical contact with the contact blocks of holder 40.

It should be apparent that there are many modifications possible with this invention. It is intended that the scope of the invention be defined by the appended claims.

Figure 6:
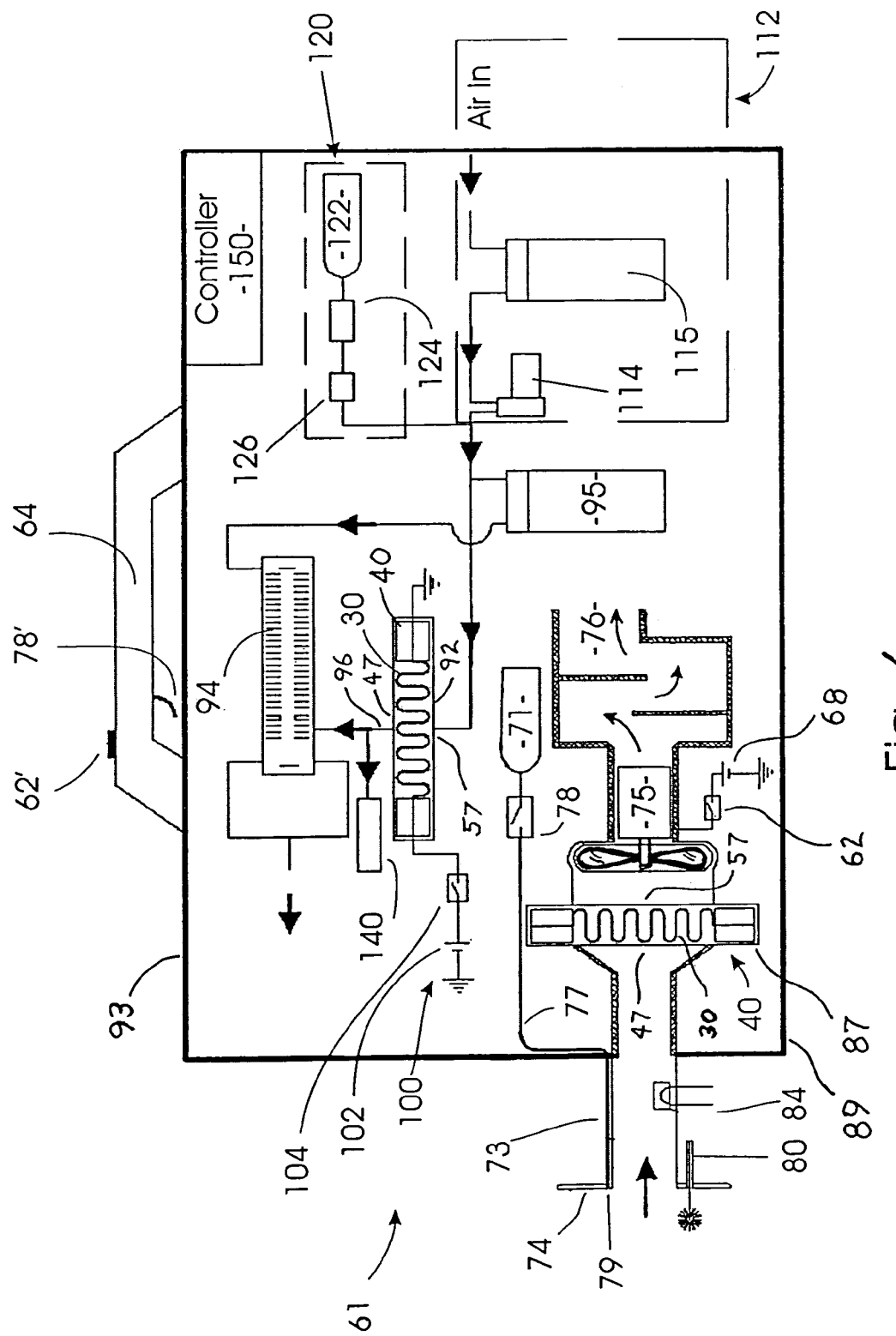
FIG. 6 is a schematic view of another embodiment of the present invention.

FIG. 6 illustrates a schematic view of another embodiment of the present invention. The reference numbers and description is the same as presented earlier for FIG. 4, with the difference being that the collection module 70 and the detection module 90 in FIG. 6 are built into one unit 61, having a single case 93.

What is claimed is:

1. A chemical detection device, comprising:
   a) a case;
   b) a chemical detector disposed within the case;
   c) a slot, disposed in the case, for receiving a substrate holder holding a porous metallic substrate contaminated with one or more target chemicals;
   d) electric heating means, disposed within the case, for resistively heating a porous metallic substrate held inside of a substrate holder that has been inserted into the detection slot, by causing electric current to flow through the substrate, whereby the flowing electricity directly heats the substrate by electric resistance heating; and
   e) means, disposed within the case, for moving a detection gas through a contaminated porous metallic substrate held inside of a substrate holder that has been inserted into the detection slot; and
   f) a substrate holder comprising:
      i) a pair of electrically-insulated, opposed panels pivotally connected to each other along one edge by a hinge, with panel latching means for clamping and tightly holding a porous metallic substrate between the panels, the substrate being electrically insulated from the panels; and
      ii) a pair of spaced electrical contacts mounted on the panels such that when the substrate is clamped and tightly held by the holder, the contacts touch the substrate and make good electrical contact;
   wherein the flow of detection gas is perpendicular to the substrate; and whereby target chemicals desorbed from the substrate are entrained into the detection gas and carried to the chemical detector for detection and analysis.

2. The device of claim 1, wherein the chemical detector comprises one or more detectors selected from the group consisting of ion mobility spectrometers, miniature ion mobility spectrometers, electron capture detectors, mass spectrometers, chemiluminescence-based systems, ChemLab-on-a-Chip detectors, and ChemLab-on-a-Chip detectors comprising chemiresistor arrays.

3. The device of claim 1, wherein the electric heating means comprises means for controllably applying a voltage difference across the pair of spaced electrical contacts mounted on the panels of the substrate holder.

4. The device of claim 3, wherein the electric heating means comprises a battery.

5. The device of claim 4, wherein the electric heating means further comprises controller means for monitoring the energy dissipated in the substrate when being heated by resistance heating by measuring current and voltage drop as a function of time; and for increasing the "on" time of the electric heating means to compensate for a decrease in the battery's voltage.

6. The device of claim 1, wherein the means for moving a detection gas comprises a fan or a container of pressurized gas.

7. The device of claim 1, further comprising a porous metallic substrate held inside of the substrate holder.

8. The device of claim 7, wherein the porous metallic substrate comprises a porous metallic sheet folded into a plurality of pleats, each pleat having a rounded cross-section.

9. The device of claim 1, wherein the panel latching means comprises one or more magnets.

10. The device of claim 1, wherein the chemical detector comprises a ion mobility spectrometer and a drift gas generating system for providing drift gas to the spectrometer.

11. The device of claim 10, wherein the ion mobility spectrometer comprises a miniature ion mobility spectrometer comprising a drift tube having an overall length of about 54 mm, a drift length of about 36 mm, and an interior diameter of about 6 mm.

12. The device of claim 1, wherein the electric heating means comprises means for heating a porous metallic substrate to a temperature within the range of 100 C to 200 C during desorption.

13. The device of claim 12, wherein the electric heating means comprises means for heating a porous metallic substrate to a temperature within the range of 150 C to 200 C during desorption.

14. The device of claim 1, wherein the total weight of the device is less than about 20 pounds, and comprises a handle for carrying the device by hand.

15. The device of claim 1, further comprising collection means, attached to the device, for exposing an uncontaminated porous metallic substrate to target chemicals during collection.

16. The device of claim 1, wherein the chemical detector comprises at least two different types of detectors.

17. The device of claim 1, further comprising a gas purifier, disposed inside of the case, for purifying detection gas before passing through a contaminated substrate.

18. The device of claim 1, further comprising means, disposed inside of the detection case, for heating the detection gas to a temperature in the range of 80 C to 100 C prior to entering the chemical detector.

19. The device of claim 1, further comprising thermal insulation surrounding the chemical detector.

20. A chemical detection device, comprising:
a) a case;
b) a collection slot, disposed within the case, for receiving a substrate holder holding a porous metallic substrate;
c) a fan, disposed within the case, for pulling air contaminated with one or more target chemicals into the case, and then through an uncontaminated porous metallic substrate, held inside a substrate holder that has been inserted into the collection slot; whereby target chemicals are deposited on the porous substrate during a collection step;
d) a chemical detector disposed within the case;
e) a detection slot, disposed in the case, for receiving a substrate holder holding a porous metallic substrate contaminated with one or more target chemicals; and
f) means, disposed within the case, for moving a detection gas through a contaminated porous metallic substrate held inside of a substrate holder that has been inserted into the detection slot;
wherein the flow of detection gas is perpendicular to the substrate; and
whereby target chemicals released from the contaminated porous metallic substrate during detection are entrained into a detection gas and carried to the chemical detector for detection and analysis; and
wherein the device further comprises electric heating means, disposed within the case, for resistively heating a contaminated porous metallic substrate held inside of a substrate holder that has been inserted into the detection slot, by causing electric current to flow through the porous metallic substrate, whereby the flowing electricity directly heats the porous metallic substrate by electric resistance heating; and
wherein the device further comprises a substrate holder comprising:
a pair of electrically-insulated, opposed panels pivotally connected to each other along one edge by a hinge, with latching means for clamping and tightly holding a porous metallic substrate between the panels, the substrate being electrically insulated from the panels; and
a pair of spaced electrical contacts mounted on the panels such that when a porous metallic substrate is clamped and tightly held by the substrate holder, the contacts touch the porous metallic substrate and make good electrical contact.

21. The device of claim 20, wherein the total weight of the device is less than about 20 pounds, and comprises a handle for carrying the device by hand.

22. A method for detecting one or more target chemicals on the surface of a contaminated object, the method comprising:
a) providing a chemical detection system according to claim 20, the system comprising a collection module and a detection module; disposed within a common case;
b) placing an uncontaminated porous metallic substrate into a substrate holder, and then inserting the substrate holder into the collection slot;
c) holding the collection module near the surface of a contaminated object and then collecting target chemicals from the surface by pulling air contaminated with target chemicals into the collection module, and then through the uncontaminated porous metallic substrate, whereby target chemicals are deposited onto the uncontaminated porous metallic substrate;

d) after the collection step has been completed, removing the substrate holder from the collection slot; and then re-inserting the substrate holder into the detection slot;

e) heating the porous metallic substrate to a temperature of between about 100 C and 200 C, by energizing the electric heating means and flowing current directly through the contaminated porous metallic substrate; thereby heating and desorbing contaminants from the porous metallic substrate; while flowing a detection gas through the porous metallic substrate; thereby entraining desorbed contaminants into the detection gas;

f) moving the detection gas with entrained contaminants to the chemical detector located inside the detection module; and g) detecting and analyzing the contaminants entrained in the detection gas.

23. A chemical detection system comprising:

a) a collection module, comprising:
  i) a collection case;
  ii) a collection slot, disposed within the collection case, for receiving a substrate holder holding a porous substrate;
  iii) a fan, disposed within the collection case, for pulling air contaminated with one or more target chemicals into the collection case, and then through an uncontaminated porous substrate held inside a substrate holder that has been inserted into the collection slot, whereby target chemicals are collected by the porous substrate during collection; and b) a detection module, comprising:
  i) a detection case;
  ii) a chemical detector disposed within the detection case;
  iii) a detection slot, disposed in the detection case, for receiving a substrate holder holding a contaminated porous substrate; and
  iv) means, disposed within the detection case, for moving a detection gas through a contaminated porous substrate held inside of a substrate holder that has been inserted into the detection slot;

wherein the flow of detection gas is perpendicular to the substrate;

whereby target chemicals released from the substrate during detection are entrained into the detection gas and carried to the chemical detector for detection and analysis;

wherein the collection module is attached removably to the detection module;

wherein the detection module comprises electric heating means, disposed within the detection case, for resistively heating a contaminated porous metallic substrate held inside of a substrate holder that has been inserted into the detection slot, by causing electric current to flow through the substrate, whereby the flowing electricity directly heats the substrate by electric resistance heating; whereby the desorption rate of target chemicals from the porous metallic substrate is increased when the substrate is heated during desorption; and wherein the system further comprises a substrate holder; wherein the substrate holder comprises:
  a pair of electrically-insulated, opposed panels pivotally connected to each other along one edge by a hinge, with latching means for clamping and tightly holding the porous metallic substrate between the panels, the substrate being electrically insulated from the panels; and
  a pair of spaced electrical contacts mounted on the panels such that when the substrate is clamped and tightly held by the holder, the contacts touch the porous metallic substrate and make good electrical contact.

24. The device of claim 23, wherein the collection module further comprises an inlet collection tube extending outward from the collection case, fluidically connected to a substrate holder disposed inside of the collection slot, with a flange mounted on the distal end of the inlet collection tube for disrupting the flow of air along the outer surface of the tube during collection.

25. The device of claim 24, further comprising gas puffing means for providing puffs of air or $CO_2$ to dislodge particles from the surface of a sample during collection.

26. The device of claim 25, further comprising a handle for holding the device, with switch means mounted on the handle for controlling the fan's operation, and trigger switch means mounted underneath the handle for activating the gas puffing means.

27. The device of claim 24, further comprising a temperature sensor for measuring the ambient air temperature.

28. The device of claim 23, wherein the fan in the collection module is battery-operated.

29. A method for detecting one or more target chemicals on the surface of a contaminated object, the method comprising:

a) providing a chemical detection system according to claim 23, the system comprising a collection module attached removably to a detection module;

b) placing an uncontaminated porous metallic substrate into a substrate holder, and then inserting the substrate holder into the collection slot;

c) holding the collection module near the surface of a contaminated object, and then collecting target chemicals from the surface by pulling air contaminated with target chemicals into the collection module, and then through the uncontaminated porous metallic substrate, whereby target chemicals are deposited onto the uncontaminated porous metallic substrate;

d) after the collection step has been completed, removing the substrate holder from the collection slot; and then re-inserting the substrate holder into the detection slot of the detection module;

e) heating the porous metallic substrate to a temperature of between about 100 C and 200 C, by energizing the electric heating means and flowing current directly through the contaminated porous metallic substrate; thereby heating and desorbing contaminants from the porous metallic substrate; while flowing a detection gas through the porous metallic substrate; thereby entraining desorbed contaminants into the detection gas;

f) moving the detection gas with entrained contaminants to the chemical detector located inside the detection module; and g) detecting and analyzing the contaminants entrained in the detection gas.

30. The method of claim 29, further comprising detaching and removing the collection module from the detection module before collecting contaminants from the surface of the contaminated object in step c).

* * * * *